United States Patent [19]

Speranza et al.

[11] Patent Number: 5,072,020

[45] Date of Patent: Dec. 10, 1991

[54] ALIPHATIC POLYAMINES FROM POLYNITRO COMPOUNDS

[75] Inventors: George P. Speranza; Michael Cuscurida; Wei-Yang Su, all of Austin, Tex.

[73] Assignee: Texaco Chemical Company, White Plains, N.Y.

[21] Appl. No.: 496,725

[22] Filed: Mar. 21, 1990

[51] Int. Cl.$^5$ .................. C07C 269/02; C07C 271/28
[52] U.S. Cl. ....................................... 560/25; 560/137
[58] Field of Search .................................. 560/25, 137

[56] References Cited

U.S. PATENT DOCUMENTS 4,816,597 3/1989 Snyder et al. .......................... 560/25
4,925,971 5/1990 Aoki et al. ........................... 560/137

Primary Examiner—Jose G. Dees
Assistant Examiner—Vera C. Clarke
Attorney, Agent, or Firm—Jack H. Park; Kenneth R. Priem; Cynthia L. Kendrick

[57] ABSTRACT

Disclosed is a novel route to diamines and triamines comprising reacting nitroalcohols with isocyanates to prepare di- and trinitro compounds which are subsequently reduced over a metal hydrogenation catalyst to the corresponding polyamino compound.

34 Claims, No Drawings

ALIPHATIC POLYAMINES FROM POLYNITRO COMPOUNDS

FIELD OF THE INVENTION

This invention relates to novel polyamino compounds which include both hard segments containing urethane groups and soft segments containing polyether groups.

More particularly this invention relates to a novel method for preparing these novel aliphatic diamines and triamines by reacting nitroalcohols with isocyanates alone or isocyanate prepolymers to prepare di- and trinitro compounds which are subsequently reduced over a metal hydrogenation catalyst to the corresponding polyamino compounds.

BACKGROUND OF THE INVENTION

There are a few methods known in the art for preparation of higher molecular weight diamines and triamines. Typical methods for preparing these compounds incorporate the use of polyether polyols.

One method involves the addition of acrylonitrile to polyols followed by hydrogenation. This can be represented as follows:

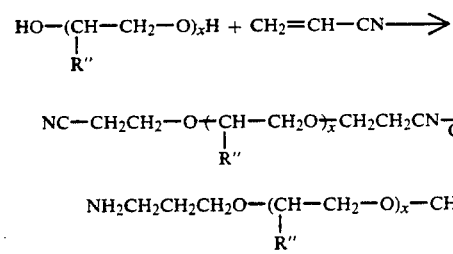

Eq.I where R" represents H, $CH_3$ or $C_2H_5$.

A second method involves the reductive amination of polyols to amines which can be represented by the following equation:

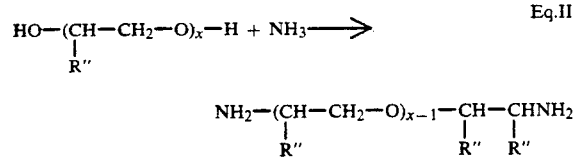

Eq.II where R" is H, $CH_3$ OR $C_2H_5$.

Polyetherpolyamines prepared by the methods described above can be used in many chemical reactions and applications. For example, they can be used in preparing other functional amine derivatives.

In U.S. Pat. No. 4,362,856 there is disclosed a method of preparing poly-(2-aminoalkyl)polyamine compounds by means of a two-step process wherein a nitroparaffin, an aldehyde and a suitable polyamine are condensed. Subsequently the poly-(2-aminoalkyl)polyamine is used to cure epoxy resins and provide products having good heat flexibility, high heat distortion temperatures and excellent solvent resistance.

U.S. Pat. No. 4,705,814 discloses the reaction product of a polyoxyalkylene polyamine and an aliphatic isocyanate which may be made rapidly without the use of heat or a catalyst.

From a survey of the related art it does not appear that it has been previously known to react nitroalcohols with isocyanate prepolymers or isocyanates to prepare di- and trinitro compounds which are reduced to polyamino compounds. The polyamino compounds are useful for the preparation of polyurea coatings and polyurea RIM products.

SUMMARY OF THE INVENTION

In accordance with the foregoing the present invention provides a method of preparing di- or trinitro compounds and reduction of the nitro compounds to polyamino compounds over a metal hydrogenation catalyst.

More specifically, there is provided a two-step method for the preparation of an aliphatic diamine or triamine which comprises reacting a nitroalcohol with some form of isocyanate to prepare di- or trinitro compounds which are reduced over a catalyst from Group VIII at a temperature of about 80° to 200° C. and pressure of atmospheric up to about 4000 psig.

DETAILED DESCRIPTION

This invention discloses novel diamines and triamines containing both hard segments containing urethane groups and soft segments containing polyether groups prepared by reacting nitroalcohols with isocyanates or isocyanate prepolymers and reducing the intermediate di- or trinitro compound.

The reaction sequence can be illustrated by the following reaction:

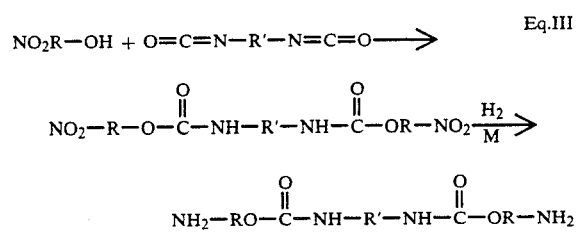

Eq.III

Where R is: an alkylene group and R' represents a di- or trifunctional isocyanate.

The first step requires the use of a nitroalcohol. Most of the nitroalcohols which are marketed commercially are formed by the condensation of formaldehyde and lower nitroparaffins. The condensation may occur one to three times, depending on the number of hydrogen atoms on the carbon with the nitro group, and yield nitroalcohols with one to three hydroxyl groups.

The nitroalcohols which can be used in the invention are those represented by the formula $HOR\text{—}NO_2$ where R is an aliphatic group, an aromatic group or an alkyl aromatic group.

Commercially available nitroalcohols include 2-nitro-1-butanol, 2-methyl-2-nitro-1-propanol, 2-methyl-2-nitro-1,3-propanediol, 2-ethyl-2-nitro-1,3-propanediol and 2-hydroxymethyl-2-nitro-1,3-propanediol. Examples 1 through 4 demonstrate the particular effectiveness of 2-methyl-2-nitro-1-propanol.

The nitroalcohols can be reacted with isocyanates or isocyanate prepolymers formed by the reaction of polyols and isocyanates. The polyols reacted with isocyanates to form prepolymers can be selected from the group consisting of polyoxypropylene glycols, polyoxyethylene glycols or mixed polyoxyethylene propylene glycols of molecular weight of about 200 to 2000, having the formula:

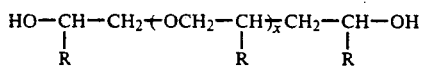

where x has a value of about 2 to 33 and R is hydrogen or methyl.

Polyols which are suitable and which are employed in the examples comprise polypropylene glycols having the formula:

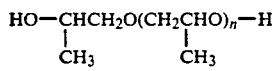

wherein n is 2–33 and the molecular weight is from about 200 to about 2000. A commercially available group of polypropylene glycols having this structure are JEFFOX® PPG products by Texaco Chemical Co.

JEFFOX® PPG 1000 is a general purpose diol with a molecular weight of about 1000. JEFFOX® PPG 2000 is a general purpose diol with a molecular weight of 2000.

By the same method triols can be reacted to form trinitro alcohols and subsequently reduced to triamines. Appropriate triols can be represented by the formula:

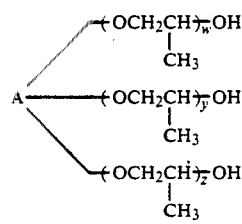

wherein A represents the nucleus of an oxyalkylation susceptible trihydric alcohol containing about 3 to 6 carbon atoms and w, y and z are numbers and the average value of the sum of w, y and z is from about 10 to about 100. An example of such a product having an average molecular weight of about 5000 is POLYOL® G-5000, a trifunctional polyether triol manufactured by Texaco Chemical Company.

As stated the nitroalcohol is reacted with an isocyanate or a prepolymer resulting from the reaction of one of the described polyols and an isocyanate.

Aromatic isocyanates and aliphatic isocyanates are suitable for use in the invention. Aromatic isocyanates are preferred. Examples of aromatic isocyanates include toluene diisocyanates, methylene diphenyl diisocyanate, hexamethylene diisocyanate and isophorone diisocyanate.

Included as aliphatic isocyanates useful in this invention are those containing aromatic characteristics but where the isocyanate moieties are attached to aliphatic portions of the molecule. Examples have structures of the following type:

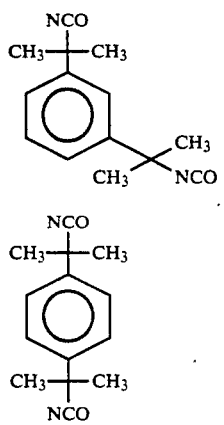

In the embodiment of the invention where a nitroalcohol is reacted with a prepolymer resulting from the reaction of a polyol and an aromatic isocyanate, the reaction can be represented as follows:

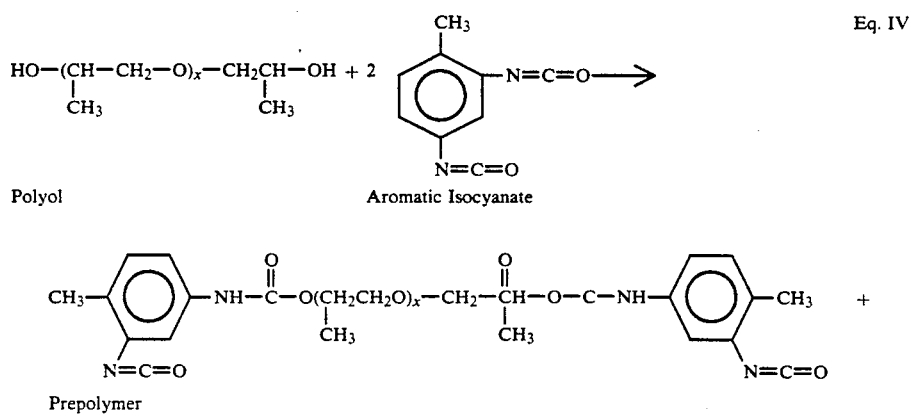

Eq. IV

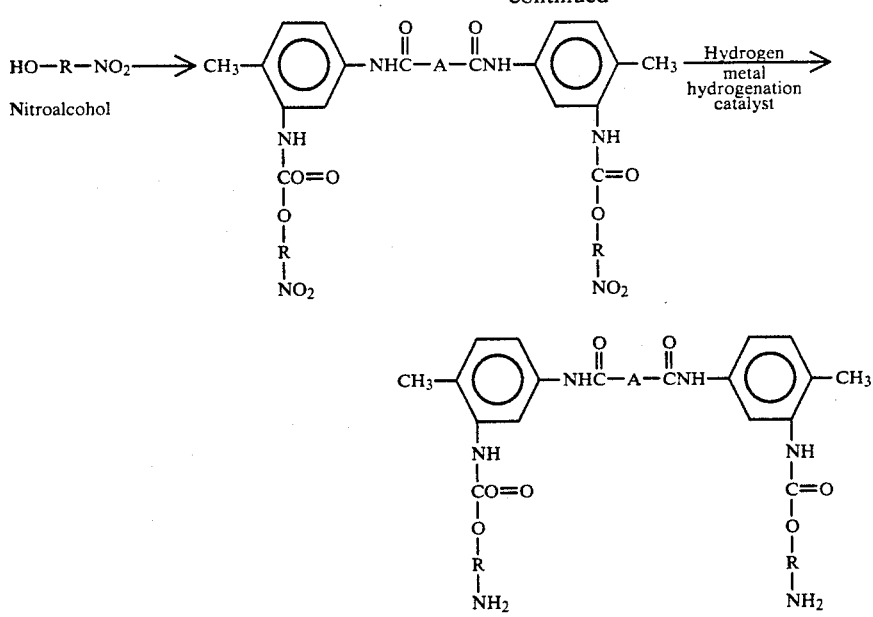

Where A=nucleus of polyoxyalkylene glycol having functionality of 2-6.

Another class of prepolymers that may be used are those prepared from diisocyanates and polyoxyalkylene diamines. In particular those prepared from polyoxyalkylene diamines and aliphatic diisocyanates. An advantage in using these products is that no tin catalyst is needed to make the prepolymer. An example of such a prepolymer is the reaction of tetramethyl xylene diisocyanate with JEFFAMINE® D-2000 amine.

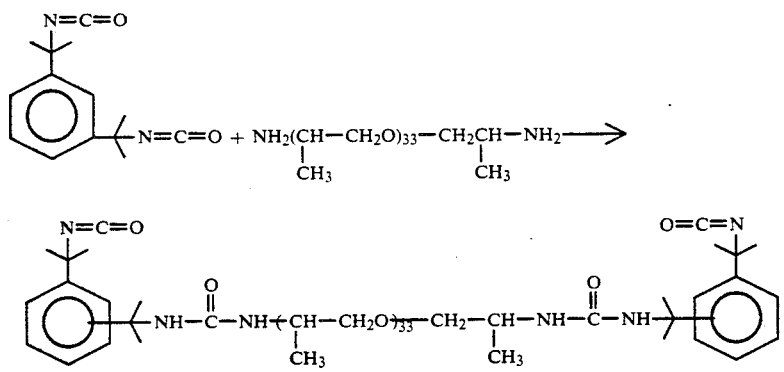

In the method of this invention, as demonstrated by the examples, a commercially available prepolymer can be reacted with the nitroalcohol or a polyol and isocyanate can be introduced into the reactor at the same time as the nitroalcohol. After the nitroalcohol and diisocyanate or prepolymer are reacted to form a di- or trinitro compound the intermediate is reduced over a metal hydrogenation catalyst.

The hydrogenation catalyst of the instant invention generally comprises one or more metals from Groups VIB, VIIB or VIII of the Periodic Table. Catalysts which can be usefully employed contain iron, cobalt, nickel, ruthenium, rhodium, palladium, platinum, chromium, molybdenum, tungsten, etc. Preferred catalysts are compounds containing nickel, palladium, cobalt or platinum. Nickel hydrogenation catalysts include Raney nickel, nickel-copper and nickel-copper-chrome. Cobalt hydrogenation catalysts include Raney cobalt, cobalt-copper and cobalt-chrome. Where palladium was used the preferred form was 1-20% palladium on a support such as charcoal.

The reaction of a nitroalcohol and a prepolymer and the reduction of the intermediate nitro compound can be carried out at a temperature of 50° C. to 200° C. The preferred temperature is about 80° C. to 120° C. The pressure can be from atmospheric to 4000 psig and is preferably from about 2000 psig to 3000 psig.

In the invention a diluent can be used and is preferable in order to facilitate mixing. Suitable diluents include methanol, ammonia, isopropanol, tertiary butyl alcohol or ethylene glycol monoethyl ether acetate.

To prepare the prepolymer two equivalents are reacted per equivalent of active hydrogen groups. The nitroalcohol and isocyanate or isocyanate prepolymer are then reacted on a 1/1 equivalent basis.

Substantially pure aliphatic di- and triamines can be separated from the reaction mixture by filtration of the catalyst and insoluble material and distillation of the solvent. Reaction products were identified by gas chromatograph, mass spectra, IR, proton NMR and elemental analysis.

In order to more fully describe the preparation and use of the novel compounds of the present invention, the following examples are given; however, such examples are presented for illustration only and are not to be construed as unduly limiting the scope of the present invention. Unless otherwise indicated, all parts and/or percentages given in these examples are by weight.

Examples 1, 2 and 3 demonstrate the preparation of dinitro compounds which can be represented by Diagrams A and B below. The structure of the product described in Example 2 is typical of the dinitro compound of Diagram A.

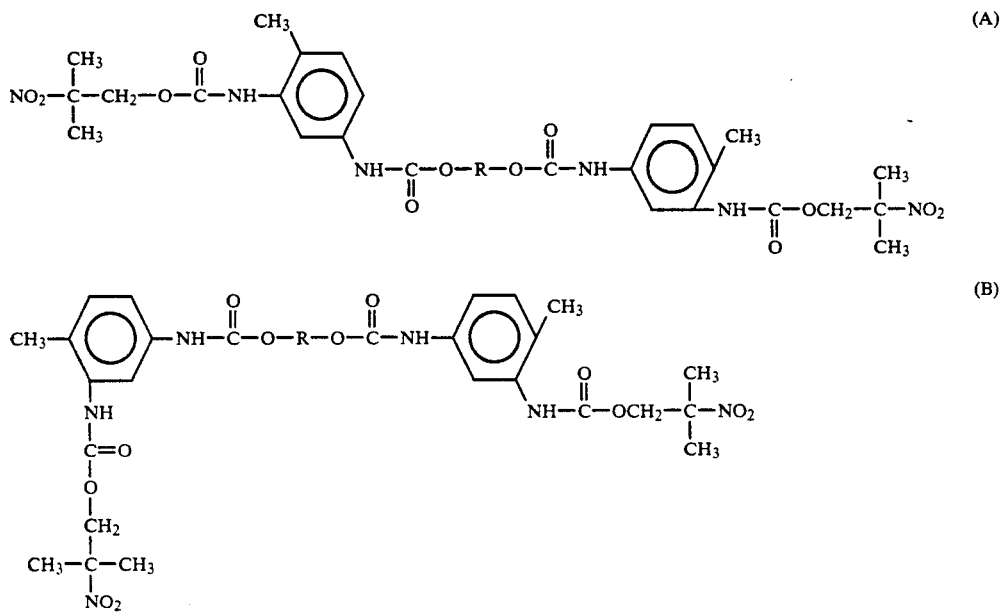

where R is the nucleus of a polyoxyalkylene glycol having a functionality of 2 to 6.

EXAMPLE 1

This example will show the preparation of a 1/1 2-nitro-2-methyl-1-propanol adduct of Mobay's Mondur CB-601 PMA polyisocyanate prepolymer. The Mondur CB-601 PMA is a toluene diisocyanate (TDI) adduct of a polyol dissolved is propylene glycol monomethyl ether acetate which has an isocyanate equivalent weight of 400.

Into a 500 ml three-necked flask equipped with a stirrer, thermometer, dropping funnel, water condenser and nitrogen source were charged 202.1 g Mondur CB-601 PMA, 60.2 g 2-nitro-2-methyl-1-propanol, 25 ml ethylene glycol monoethyl ether acetate and 0.02 g dibutyl tin dilaurate. The reaction mixture was then heated to 100–110° C. and held at that temperature for 3 hours. The resultant product was a yellow viscous liquid. The infrared spectra showed only trace quantities of unreacted isocyanate groups at ≈2280 cm-1.

EXAMPLE 2

This example will illustrate the preparation of a 1/2/1 1000 m.w. polypropylene glycol adduct of PPG-1000/TDI and 2-methyl-2-nitro-1-propanol.

Into a 500 ml three-necked flask, equipped as in Example 1, were charged 250 g of PPG-1000, 87 g TDI and 0.1 g dibutyltin dilaurate. The temperature rapidly rose to 63° C. and then dropped to 48° C. after 1 hour. Ethylene glycol monoethyl ether acetate (50 ml) and 2-methyl-2-nitro-1-propanol (59.6 g) were then charged into the reaction mixture which was then heated at 60°–70° C. for 1.3 hours. The resultant product was a yellow viscous liquid which contained only trace quantities of free isocyanate. The NMR spectra of the product verified the following structure:

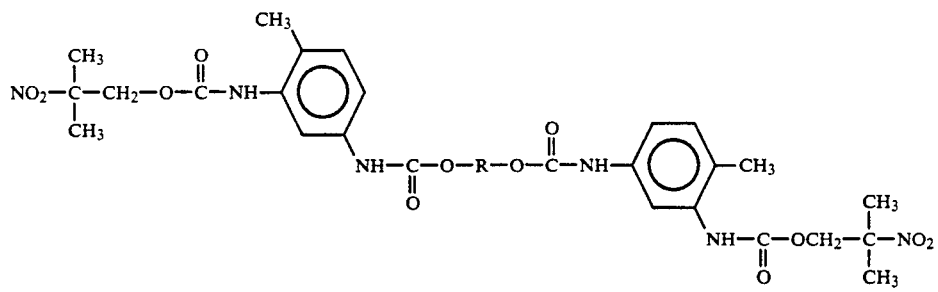

where R represents the reaction product residue of PPG-1000.

EXAMPLE 3

This example will demonstrate the preparation of a 1/2/1 adduct of a 2000 m.w. polypropylene glycol (PPG-2000)/TDI/and 2-methyl-2-nitro-1-propanol.

Into a 1000-ml three-necked flask equipped as in Example 1, were charged 69.6 g TDI, 100 ml ethylene glycol monoethyl ether acetate, and 0.2 g dibutyltin dilaurate. PPG-2000 (400 g) was then added dropwise over a 2.25 hour period. The exotherm peaked at 38° C. during that time. The reaction mixture was subsequently heated to 93° C. and held at that temperature for approximately ½ hour. 2-methyl-2-nitro-1-propanol (47.65 g) was then charged into the reaction mixture which was heated an additional hour at 92°–93° C. The product was then diluted with an additional 171 g ethylene glycol monoethyl ether acetate. The final product was a yellow viscous liquid which contained only trace quantities of free isocyanate.

EXAMPLE 4

To a 1 liter stirred autoclave was added 144 g of product made from toluene diisocyanate, polypropylene glycol 1000, and 2-nitro-2-methyl-propanol (Example 2) and 100 g of isopropanol solvent along with a nickel hydrogenation catalyst. The solution was hydrogenated at 100°–120° C. and 2300–2400 psig hydrogen pressure until there was no further drop in pressure. Most of the solvent and water was removed and the product analyzed. The total amine assay was 0.908 meq/gram and the primary amine content was 0.896 meq/gram. Infrared and NMR spectrum agreed well with the following proposed structure:

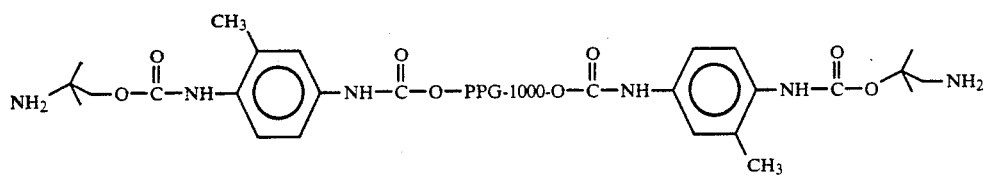

EXAMPLE 5

The product prepared in Example 1 was hydrogenated in 1 liter stirred autoclave. To the autoclave was added 130 g of product prepared in Example 1, 160 g of methanol and 19.5 g of 5% Pd on Charcoal. The reactants were hydrogenated at 110° C. and 2450 psig of hydrogen. After removing most of the solvent the total amine content was 2.133 meq/g while the primary content was 2.093 meq/g.

EXAMPLE 6

The product prepared in Example 2 was hydrogenated over a cobalt hydrogenation catalyst at 2500 psig hydrogen pressure and 140° C. The product with solvent was analyzed as having a total amine content of 0.632 meq/g and a primary amine content of 0.622 meq/g.

EXAMPLE 7

The product prepared in Example 3 was hydrogenated over a nickel hydrogenation catalyst at 140°–150° C. and 2400–2500 psig of hydrogen. The product, containing some solvent, had an amine content of 0.415 meq/g with a primary amine content of 0.392 meq/g.

EXAMPLE 8

This example will illustrate the use of the hydrogenated derivative of Example 2 in the preparation of blocked isocyanate coatings. The blocked isocyanate was prepared by reaction of Mobay's 601 PMA polyisocyanate adduct with an equivalent quantity of methyl ethyl ketone oxime. It had an isocyanate equivalent of 543.6.

Formulations, details of preparation and film properties are shown in the following table.

| Sample Number Formulation, pbw | |
|---|---|
| Methyl ethyl oxime-blocked isocyanate prepolymer[a] | 13.2 |
| Hydrogenated product of Example 2[b] | 26.8 |
| t-butanol | 3.4 |
| Details of preparation | |
| Wet film thickness, mil | 5 |
| Cure temperature, °C. | 100–105 |
| Cure time, hr. | 0.5 |
| Properties | |
| Pencil hardness | <3 B |
| Impact resistance, in./lb | |
| Forward | Pass 160 |
| reverse | Pass 160 |

[a]Isocyanate equivalent weight 543.6
[b]Amine content, meq/g 0.908

EXAMPLE 9

This example will demonstrate the reactivity of the hydrogenated derivative of Example 2 with Isonate 143L (a liquid MDI supplied by Dow Chemical Co.).

The hydrogenated derivative of Example 2 (20 g) and Isonate 143L (2.63 g) when mixed with a wooden spatula gelled immediately to a tough, flexible, elastomeric-like material.

What is claimed is:
1. A method for preparing a diamine or triamine which comprises reacting a nitroalcohol and a compound selected from the group consisting of an isocyanate or isocyanate prepolymer to form a nitro compound and passing the resulting nitro compound over a metal hydrogenation catalyst to produce the corresponding diamine or triamine.
2. The method of claim 1 wherein the diamine is an aliphatic diamine.
3. The method of claim 1 wherein the triamine is an aliphatic triamine.
4. The method of claim 1 wherein the nitroalcohol is represented by the formula:

HOR—NO2 where R is an aliphatic, aromatic or alkyl aromatic group.
5. The method of claim 4 wherein the nitroalcohol is selected from the group consisting of 2-nitro-1-butanol and 2-methyl-2-nitro-1-propanol.
6. The method of claim 4 wherein the nitroalcohol is 2-methyl-2-nitro-1-propanol.
7. The method of claim 1 wherein the isocyanate is selected from the group consisting of aromatic or aliphatic isocyanates.
8. The method of claim 1 wherein the isocyanate is an aromatic isocyanate.

9. The method of claim 1 wherein the isocyanate is selected from the group consisting of toluene diisocyanate, methylene diphenyl diisocyanate, hexamethylene diisocyanate, isophorone diisocyanate, and tetramethylxylene diisocyanate.

10. The method of claim 9 wherein the isocyanate is toluene diisocyanate, and tetramethylxylene diisocyanate.

11. The method of claim 1 wherein the isocyanate prepolymer is formed by the reaction of an isocyanate and a polyol of the formula:

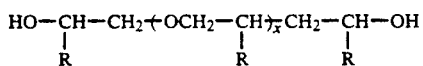

where R is hydrogen, methyl, or ethyl and x has a value of about 2 to 33.

12. The method of claim 1 wherein the isocyanate prepolymer is formed by the reaction of an isocyanate and a polyol of the formula:

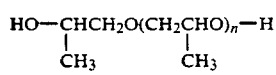

wherein n is 2 to 33 and the molecular weight is from 200 to 2000.

13. The method of claim 12 wherein the molecular weight is about 1000.

14. The method of claim 12 wherein the molecular weight is about 2000.

15. The method of claim 1 wherein the hydrogenation catalyst is selected from the group consisting of a nickel-containing catalyst, palladium-containing catalyst, cobalt containing catalyst and platinum-containing catalyst.

16. The method of claim 1 wherein the temperature is between 50°-200° C.

17. The method of claim 1 wherein the temperature is between 80° and 130° C.

18. The method of claim 1 wherein the pressure is between 1 psig and 4000 psig.

19. The method of claim 18 wherein the pressure is between 2000 psig and 3000 psig.

20. An amine containing a urethane linkage represented by the structure:

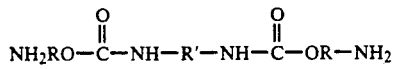

where R is an alkylene group having 2 to 5 carbons and R' is an aromatic group.

21. A diamine of the formula:

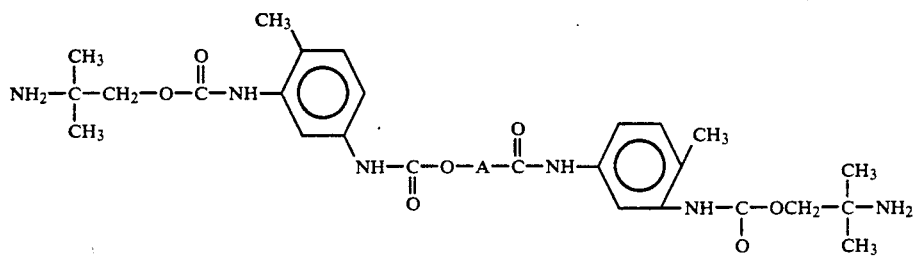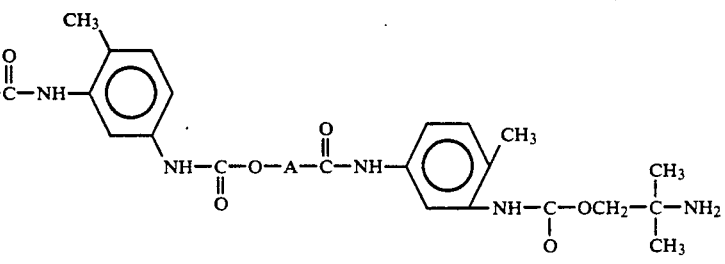

where A is the reaction product residue of a polyoxyalkylene group which can be represented by:

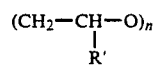

where R' is hydrogen, methyl or ethyl and n is 2 to about 33.

22. A diamine of the formula:

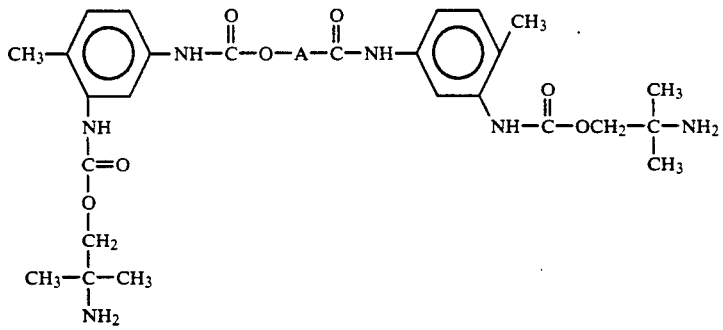

where A is the reaction product residue of a polyoxyalkylene group which can be represented by:

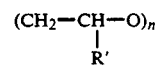

where R' is hydrogen, methyl or ethyl and n is 2 to about 33.

23. A polyamino compound comprising a reduced polynitro compound wherein the polynitro compound is the reaction product of a nitroalcohol and an isocyanate-containing compound.

24. The compound of claim 23 wherein the isocyanate is selected from the group consisting of aromatic and aliphatic isocyanates.

25. The compound of claim 23 wherein the isocyanate is an aromatic isocyanate.

26. The compound of claim 23 wherein the isocyanate is selected from the group consisting of toluene diisocyanate, methylene diphenyl diisocyanate, hexamethylene diisocyanate and isophorone diisocyanate, and tetramethylxylene diisocyanate.

27. The compound of claim 23 wherein the isocyanate is toluene diisocyanate.

28. The compound of claim 23 wherein the isocyanate-containing compound is an isocyanate prepolymer resulting from the reaction of a polyol and an isocyanate.

29. The compound of claim 28 wherein the polyol is a polypropylene glycol of the formula:

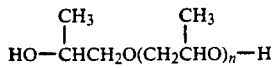

wherein n is 2 to 33 and the molecular weight is from about 200 to about 2000.

30. The compound of claim 29 wherein the molecular weight of the polypropylene glycol is about 1000.

31. The composition of claim 29 wherein the molecular weight of the polypropylene glycol is about 2000.

32. The compound of claim 23 wherein the isocyanate-containing compound is a prepolymer formed from an isocyanate and a polyol which is a trifunctional polyether triol having the formula:

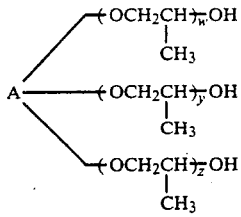

wherein A represents the nucleus of an oxyalkylation susceptible trihydric alcohol containing about 3 to 6 carbon atoms and w, y and z are numbers and the average value of the sum of w, y and z is from about 10 to about 100 and having an average molecular weight of about 5000.

33. The compound of claim 23 wherein the nitroalcohol has the formula HOR—NO$_2$ where R is selected from the group consisting of aliphatic, aromatic and alkyl aromatic groups.

34. The compound of claim 23 wherein the nitroalcohol is 2-methyl-2-nitro-1-propanol.

* * * * *